United States Patent [19]

Ryan

[11] Patent Number: 5,460,797
[45] Date of Patent: Oct. 24, 1995

[54] METHOD FOR FIXING TISSUES AND CELLS FOR ANALYSIS USING OXAZOLIDINE COMPOUNDS

[75] Inventor: Wayne L. Ryan, Omaha, Nebr.

[73] Assignee: Streck Laboratories, Inc., Omaha, Nebr.

[21] Appl. No.: 333,875

[22] Filed: Nov. 3, 1994

Related U.S. Application Data

[63] Continuation of Ser. No. 52,648, Apr. 26, 1993, abandoned, which is a continuation-in-part of Ser. No. 696,926, May 8, 1991, Pat. No. 5,196,182, and a continuation-in-part of Ser. No. 877,738, May 4, 1992, Pat. No. 5,260,048, and a continuation-in-part of Ser. No. 943,359, Sep. 10, 1992.

[51] Int. Cl.$^6$ ....................................... G01N 1/28
[52] U.S. Cl. ...................... 435/40.5; 422/40; 435/40.51; 435/40.52
[58] Field of Search ............................. 424/3, 75; 422/40

[56] References Cited

U.S. PATENT DOCUMENTS

| | | | |
|---|---|---|---|
| 2,554,944 | 5/1951 | Ferrari | 8/94.11 |
| 3,862,300 | 1/1975 | Wertlake et al. | 424/3 |
| 4,064,055 | 12/1977 | Carney | 252/8.5 C |
| 4,099,917 | 7/1978 | Kim | 23/230 B |
| 4,160,644 | 7/1979 | Ryan | 23/230 B |
| 4,205,059 | 5/1980 | von Hagens | 427/4 |
| 4,219,440 | 8/1980 | Runck et al. | 252/408 |
| 4,287,087 | 9/1981 | Brinkhous et al. | 252/408 |
| 4,348,201 | 9/1982 | Hayashi et al. | 8/94.18 |
| 4,404,181 | 9/1983 | Mauthner | 424/3 |
| 4,493,821 | 1/1985 | Harrison | 424/3 |
| 4,578,282 | 3/1986 | Harrison | 422/57 |
| 4,652,449 | 3/1987 | Ropars et al. | 424/101 |
| 4,666,699 | 5/1987 | Slifkin | 424/7.1 |
| 4,698,312 | 10/1987 | Wong et al. | 436/10 |
| 4,704,364 | 11/1987 | Carver et al. | 436/10 |
| 4,705,799 | 11/1987 | Gregory | 514/376 |
| 4,762,522 | 8/1988 | Maue | 8/94.19 R |
| 4,767,206 | 8/1988 | Schwartz | 356/73 |
| 4,774,189 | 9/1988 | Schwartz | 436/10 |
| 4,793,994 | 12/1988 | Helioff et al. | 424/71 |
| 4,839,087 | 6/1989 | Tufts | 252/182.27 |
| 4,841,064 | 6/1989 | Gaglani et al. | 548/215 |
| 4,844,891 | 7/1989 | Rosen et al. | 424/76.4 |
| 4,848,377 | 7/1989 | Bires et al. | 132/222 |
| 4,867,908 | 9/1989 | Recktenwald et al. | 252/408.1 |
| 4,876,189 | 10/1989 | Schetters et al. | 435/7 |
| 4,880,602 | 11/1989 | Al-Sioufi | 422/28 |
| 4,882,284 | 11/1989 | Kirchanski et al. | 436/63 |
| 4,918,004 | 4/1990 | Schwartz | 435/7 |
| 4,931,385 | 6/1990 | Block et al. | 435/7 |
| 4,946,669 | 8/1990 | Siegfried et al. | 424/4 |
| 4,962,038 | 10/1990 | Carter et al. | 436/10 |
| 4,980,176 | 12/1990 | Berke et al. | 424/682 |
| 4,987,086 | 1/1991 | Brosnan et al. | 436/501 |
| 5,034,222 | 7/1991 | Kellett et al. | 424/76.4 |
| 5,037,843 | 8/1991 | Schoenberg | 514/389 |
| 5,059,518 | 10/1991 | Kortright et al. | 435/6 |
| 5,073,623 | 12/1991 | Prantel et al. | 530/210 |
| 5,091,174 | 2/1992 | Lemberger | 424/75 |
| 5,106,744 | 4/1992 | Kass | 435/240.2 |
| 5,112,871 | 5/1992 | Austin | 514/727 |
| 5,118,713 | 6/1992 | Donofrio et al. | 514/709 |
| 5,153,067 | 10/1992 | Yoshida et al. | 428/402 |
| 5,260,048 | 11/1993 | Ryan | 424/3 |

FOREIGN PATENT DOCUMENTS

| | | |
|---|---|---|
| 0433516 | 6/1991 | European Pat. Off. . |
| 0469766 | 2/1992 | European Pat. Off. . |
| 3821678 | 1/1990 | Germany . |
| 8500379 | 1/1985 | WIPO . |
| WO9117436 | 11/1991 | WIPO . |
| 9406290 | 3/1994 | WIPO . |

OTHER PUBLICATIONS

Semple, John W. et al., "Rapid Separation of CD4+ and CD19+ Lymphocyte Populations From Human Peripheral Blood by a Magnetic Activated Cell Sorter (MACS)[1]," Cytometry 14:955–960 (1993).

McCarthy, D. A. et al., "A Simple Flow Cytometric Procedure for the Determiniation of Surface Antigens on Unfixed Leucocytes in Whole Blood," J. Immunol. Meth. 163:155–160 (1993).

Eachus, K. et al., "Nitroparaffin–Derived Heterocyclic Antimicrobial Compounds," SOFW 9:337–342 (1991).

Tome, Y. et al., "Preservation of Cluster 1 Small Cell Lung Cancer Antigen in Zinc–Formalin Fixative and its Application to Immunohistological Diagnosis," Histopathal 16:469–474 (1990).

Jones, M. J. et al., "Transition Metal Salts as Adjuncts to Formalin for Tissue Fixation," Laboratory Investigations 44:32A (1981).

"Cosmetics and Drug Preservation," Kobava, J. ed., pp. 177–178, 647 and 657–659.

Bagwell, C. B., "Clinical Data Analysis for Flow Cytometry," Flow Cytometry (Keran) (1989).

Histochoice™ Tissue Fixative, Clinical Lab Products (Aug. 1992).

Product data sheet: TB47 Angus (1988).
Product data sheet: TB54 Angus (1990).
Product data sheet: TDS10 Angus (1991).
Product data sheet: TDS28 Angus (1992).
Product data sheet: TDS30 Angus (1989).
Product data sheet: TDS40 Angus (1991).
Product data sheet: TDS41 Angus (1991).
Product data sheet: HULS (1990).

(List continued on next page.)

Primary Examiner—Marian C. Knode
Assistant Examiner—S. Saucier
Attorney, Agent, or Firm—Harness, Dickey & Pierce

[57] ABSTRACT

A method and composition for fixing and stabilizing tissues, cells, and cell components such that the antigenic sites are preserved for a useful period of time. The fixative employs compounds that are less toxic, non-flammable, and that stabilize the cell with minimal damage to and alteration of the cell morphology. In particular, the cell antigenic sites are left intact so that studies with monoclonal antibodies may be conducted. The invention also discloses a method for developing a positive control for test reagents and for test instrumentation.

10 Claims, 7 Drawing Sheets

OTHER PUBLICATIONS

Product data sheet: HULS Nuosept 65 (Sep. 10, 1991).
Product data sheet: HULS Nuosept 95 (1989).
Product data sheet: HULS Nuosept 145 (1990).
Keren, D. F., "Flow Cytometry in Clinical Diagnosis" (1989).

METHOD FOR FIXING TISSUES AND CELLS FOR ANALYSIS USING OXAZOLIDINE COMPOUNDS

CROSS-REFERENCE TO RELATED APPLICATIONS

The present application is a continuation of U.S. patent application Ser. No. 08/052,648, filed Apr. 26, 1993 now abandoned which is a continuation-in-part of the following applications:

| U.S. Ser. No. | Filing Date | Inventor |
| --- | --- | --- |
| 07/696,926 | 8 May 1991 | Wayne L. Ryan now U.S. Pat. No. 5196182 |
| 07/877,738 | 5 May 1992 | Wayne L. Ryan now U.S. Pat. No. 5260048 |
| 07/943,359 | 10 Sep 1992 | Wayne L. Ryan |

Each of the foregoing listed applications is hereby incorporated by reference in its entirety.

TECHNICAL FIELD

The present invention generally relates to solutions containing compositions useful in the stabilization and fixation of cells, tissues and intracellular substances. More particularly, to compositions that also preserve antigenic sites for a useful period of time. The present invention also describes a process for stabilizing the antigenic sites of cells or cell components. Also disclosed, as a further aspect of the invention, are processes for utilizing cells or cell components for use in histological studies and the like.

BAKGROUND ART

In biological and biochemical analysis, and related arts, it is often necessary to store and preserve biological tissues, such as cells, cell components, proteins, and certain organic components thereof, for useful periods of time. Such biological materials are often utilized in a wide variety of applications, including but not limited to instructional aids and the diagnosis and treatment of diseases. For example, certain organisms and components thereof are often preserved in or by solutions for use in the learning arts. Likewise, such biological materials are often utilized in histological, cytological, immunological, and proteinaceous studies and the like.

Thus, it is desirable in the art to obtain a fixative or stabilizing solution which may be utilized to not only perform all the results obtainable by prior fixative or stabilizing solution, but to also provide a solution capable of preserving antigenic sites.

While the objects of any "preservative" utilized in fixing or stabilizing biological materials varies and depends upon the intended use of the "preserved" material, certain materials are known in the art for securing some desirable results. Thus, the present invention relates to compositions for the fixing of cells and tissues and to methods for fixing cells and tissues using as the fixing agent certain reagents.

The primary objective of tissue fixation is to provide as much structural detail of cells and components thereof as possible. To do this, it is necessary to maintain the cells in their original unaltered morphology so that maximum cellular detail may be observed. With the clinical application of immunostaining, there is also the requirement that antigens are not altered by the method of fixation or stabilization. Although the microscope is still the conventional means for examining fixed and stained biological materials, biological materials may also be examined with a flow cytometer. The flow cytometer is an important method for examining a plurality of cells in a brief time.

The usual formulations for stabilization of cells contain one or more agents which react vigorously with the proteins of the cells to denature and insolubilize the components of the cell. Typical of this type of agent is picric acid, mercuric ions, formaldehyde and glutaraldehyde. In addition, some less toxic compounds can also be utilized which denature and stabilize the proteins such as acetic and formic acid.

Unfortunately, the toxicity associated with such compounds renders their use less than satisfactory. For example, a 37% solution of formaldehyde, the most common of these fixatives, is a noxious gas which is also toxic, flammable, and carcinogenic.

Although efforts are made when this chemical is used to protect workers and avoid contamination of the drainage system when disposed, these efforts are usually both expensive and inconvenient, and fixatives such as formaldehyde still present a danger to laboratory workers and health care professionals. Thus, it is highly desirable to develop fixatives which can be used safely, effectively and conveniently in histological studies.

Also known in the art are various methods for analyzing histological, cytological, immunological, and proteinaceous materials. For example, surface marker analysis has developed as a laboratory tool which is particularly useful for clinical diagnosis through the investigation of immunodeficiency states, differentiation of cell types and development stages, and other cell processes. The expansion of uses for surface marker analysis has resulted in the use of flow cytometry and antibody probes to evaluate cellular properties. While other means of assaying for surface marker analysis exist, flow cytometry provides rapid, objective and quantitative assessment of surface markers.

Flow cytometry and flow cytometers are generally described in Keran's text, Flow Cytometry in Clinical Diagnosis (1989). Flow cytometers operate in principle by multiparameter analysis of heterogeneous cell populations (or cellular components) on a cell-by-cell basis. Flow cytometry allows biological and physical properties of cells and cellular components to be determined.

In flow cytometry, cells in suspension are forced single file, via hydrodynamic focusing, through the path of a laser beam. Interaction of the cells with the laser beam scatters some of the light and causes excitation and emission from fluorescent molecules present on the surface or interior of the cell. A series of lenses collect the scattered or emitted light and pass it to a photomultiplier. Each photomultiplier measures a separate parameter. Parameters measured include: forward light scatter, which measures relative particle size; side light scatter, which measures relative granularity or other internal structure; and fluorescence emission. The optical signals are converted by a computer to a data display for analysis and interpretation.

A chromophore may be applied to a cell suspension or the cells may be labeled with monoclonal antibodies which have been conjugated directly or indirectly with fluorochromes. These probes are usually specific for a surface antigen or some intracellular substance of interest, such as DNA. The choice of the probe depends on the diagnostic or biological parameter of clinical interest.

Compounds typically used to stabilize cells may preserve some cellular antigens though certain antigens are more sensitive to loss of reactivity to monoclonal antibodies. Examples of such antigens are the cluster designation antigens (CD) present on the surface of hematopoietic cells. Much of the clinically useful applications of surface marker analysis, and much of the development of the surface marker assay technology, has focused on lymphocyte CD markers. It should be noted that intracellular substances such as nucleic acids can be liberated from cells and stabilized by the addition of the presently described fixative agent. The stabilized nucleic acids can be used for example in PCR-based in situ hybridization.

Another problem with the use of existing compounds which stabilize cells for analysis is that certain critical antigens are present in small quantities, thus they are not detectable even if only a small percentage of these antigens are destroyed.

Therefore, it is an object of the invention to provide a fixative solution for tissues cells, or intracellular substance which has an extremely low toxicity yet meets all of the requirements of a model fixative.

Another object of the invention is to provide a fixative solution for tissues, cells or intracellular substances that preserves cellular detail. This fixative solution is made by the process of:

a) suspending material to be fixed or stabilized in an agent; said agent comprising an active agent in a solution, said active agent: (a) containing formaldehyde as an equilibrium component, (b) can be synthesized from formaldehyde, (c) functions to fix or stabilize with from between 5 to 100 grams of agent per liter; (d) are chemical disinfectants and (e) are capable of undergoing hydrogen bonding.

Another object of the present invention is to provide a fixative which in addition to being low in toxicity gives off no noxious fumes, is not flammable or carcinogenic, and which can be disposed of safely and conveniently.

Yet another object of the invention is to provide a fixative solution for tissues and cells that preserves tissues and cells and their antigenic detail to allow for the satisfactory conducting of immunohistochemical and other immunological techniques on the tissues and cells.

Yet another object of the invention is to provide a fixative solution that provides an unaltered antigenic surface for reaction with specific antibodies.

Yet another object of the invention is to provide cytological controls for use in biological analysis and studies. These and other objects of the invention are obtained by a fixative solution for tissues and cells comprising histological fixing amounts of at least one active agent selected from the group consisting of:

i) diazolidinyl urea, ii) imidazolidinyl urea, iii) dimethylol-5,5-dimethylhydantoin, iv) dimethylol urea, v) 2-bromo-2-nitropropane-1,3-diol, vi) oxazolidines, vii) sodium hydroxymethyl glycinate.

In another aspect, the invention comprises an improvement in a method of fixing tissues and cells with a histological fixative wherein the histological fixative is an active agent selected from at least one of the group consisting of:

i) diazolindinyl urea, ii) imidazolidinyl urea, iii) dimethylol-5,5-dimenthylhydantoin, iv) dimethylol urea, v) 2-bromo-2-nitropropane-1,3-diol, vi) oxazolidines, vii) sodium hydroxymethyl glycinate.

Figure 1:
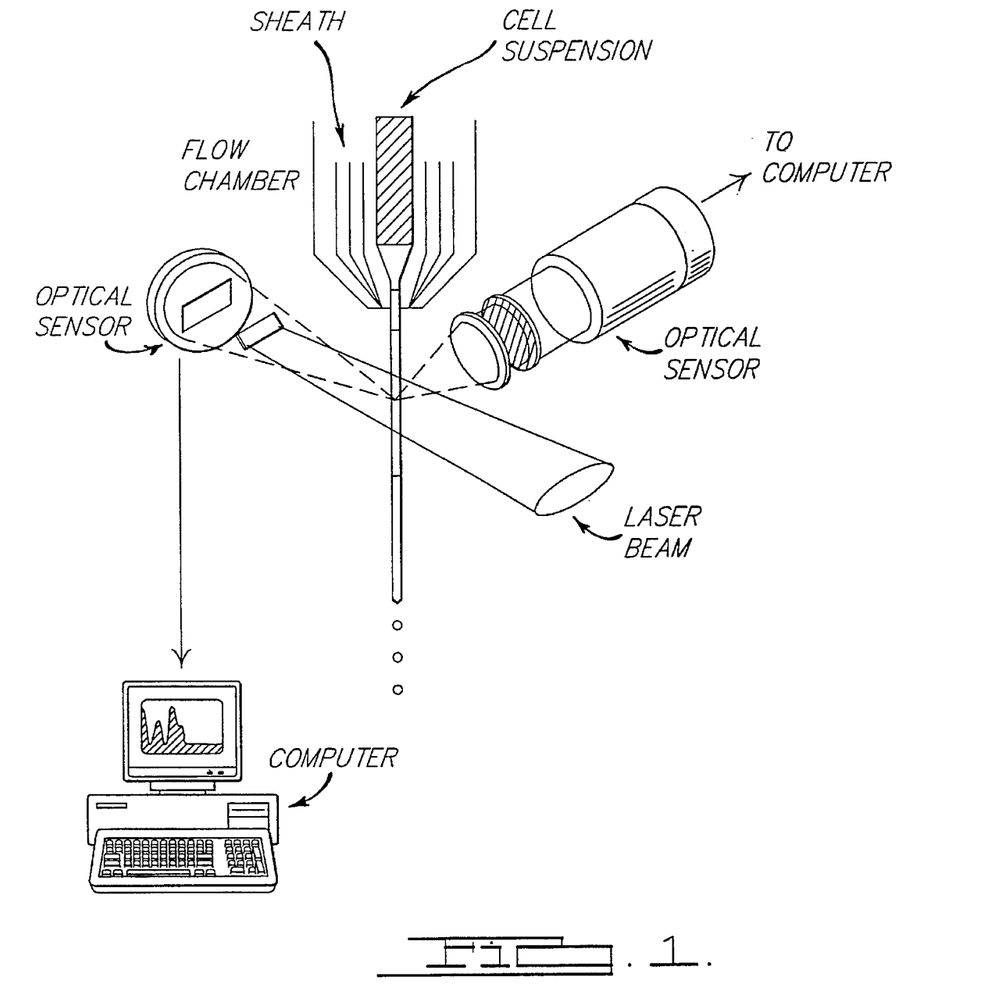
FIG. 1 is a schematic diagram of a flow cytometer.
Figure 2:
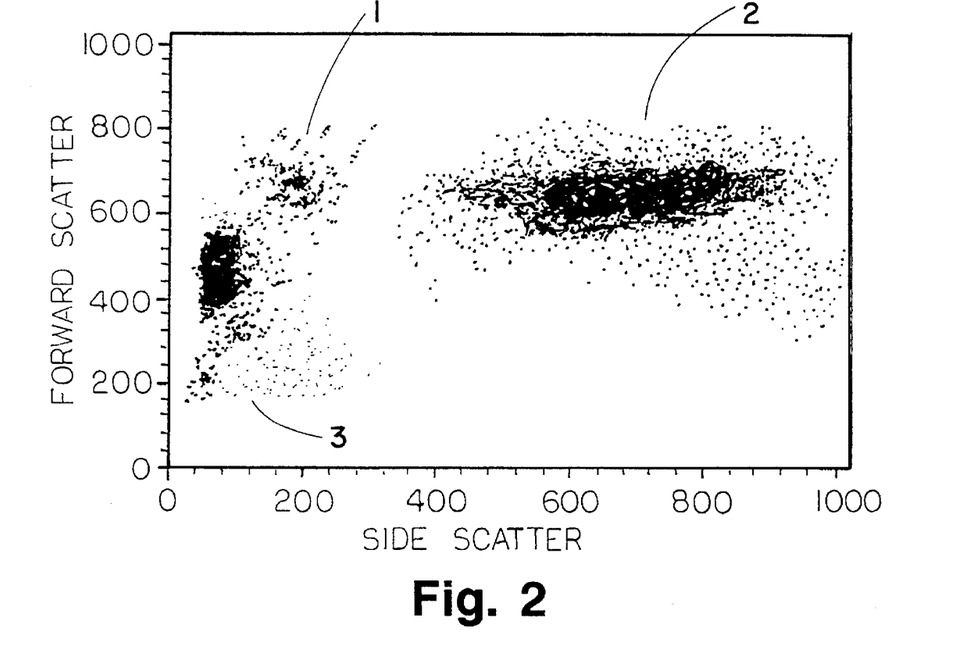
FIG. 2 is a graphical illustration of a flow cytometry scattergram wherein the enumeration of subsets is given, and wherein monocytes 1, granulocytes 2, and lymphocytes 3 are illustrated.
Figure 3:
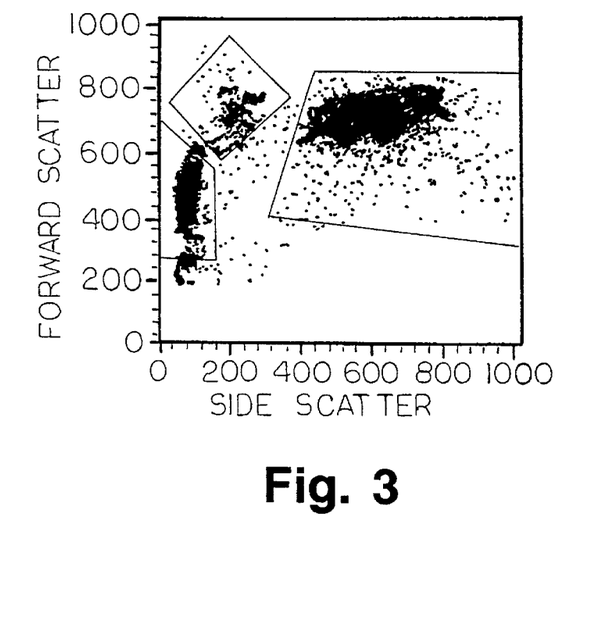
FIG. 3 is a graphical illustration of the same scattergram as illustrated in FIG. 2 wherein the subsets are "gated;"
Figure 4A:
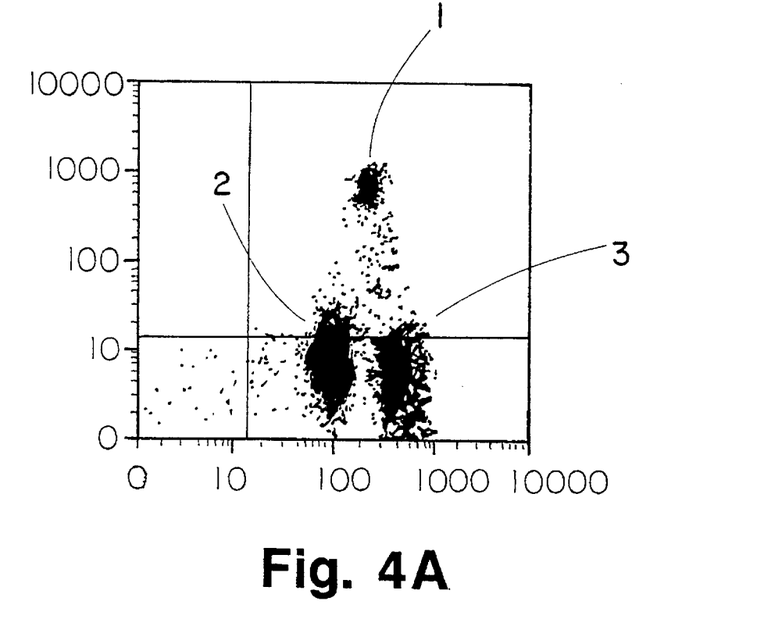
FIGS. 4A and 4B are graphical illustrations of dot plots wherein phenotyping of subsets was accomplished by means of fluorescence.
Figure 4B:
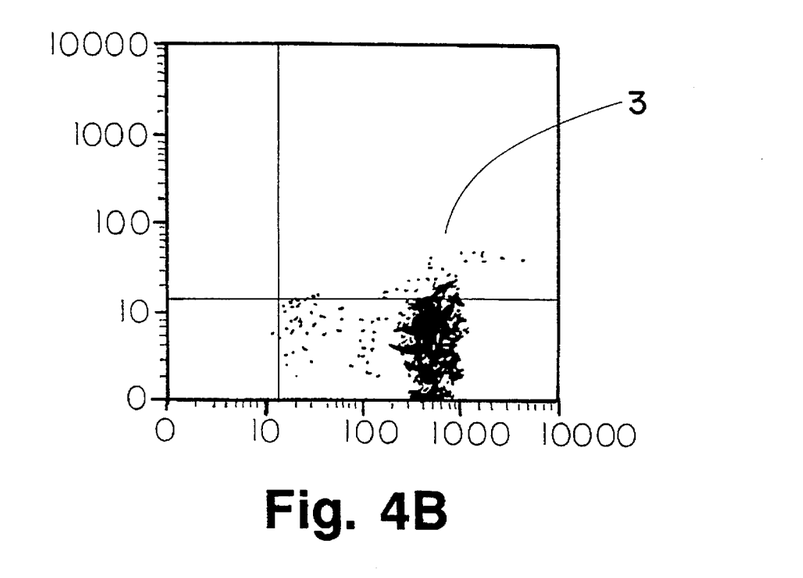
Figure 5:
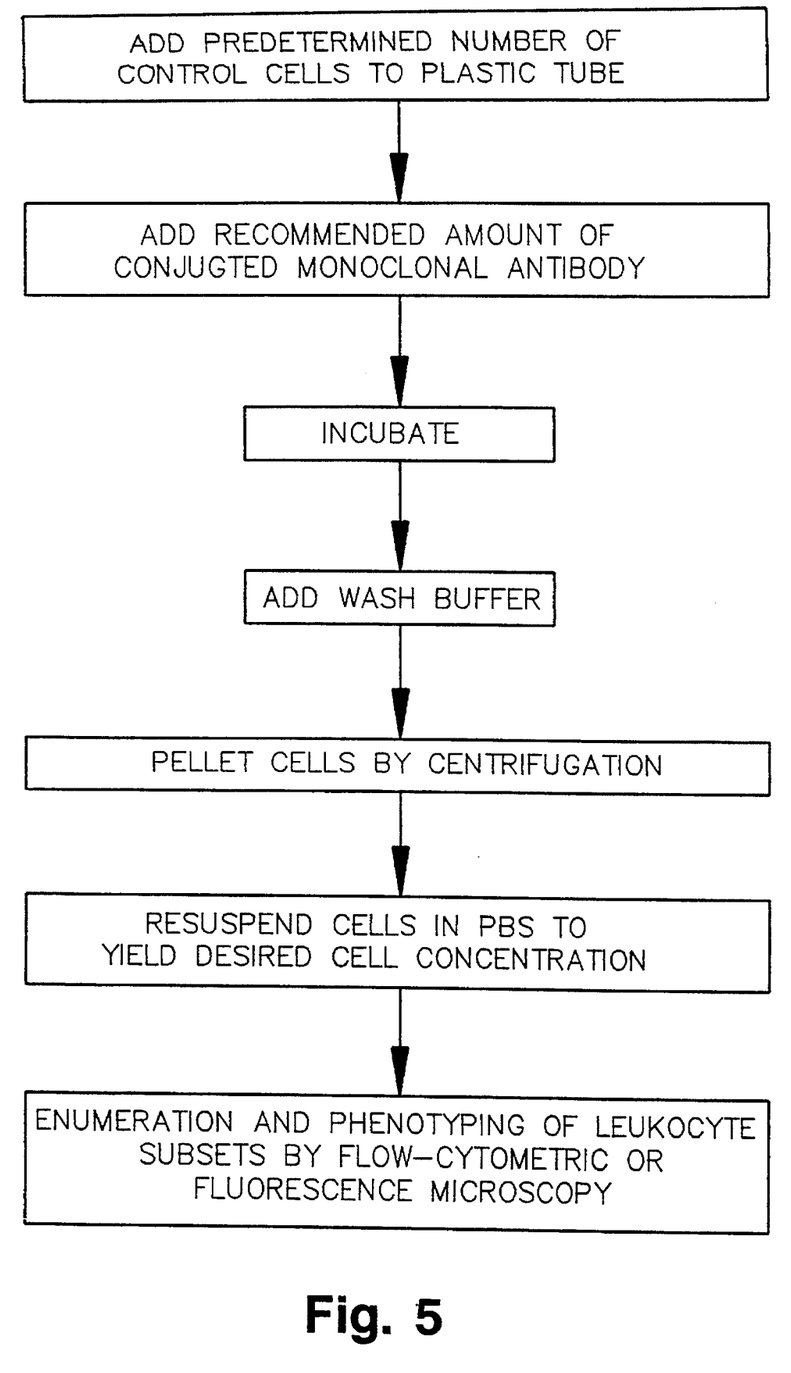
FIG. 5 is a flow diagram illustrating the procedure for preparing stabilized leukocytes for antigen-antibody studies.
Figure 6:
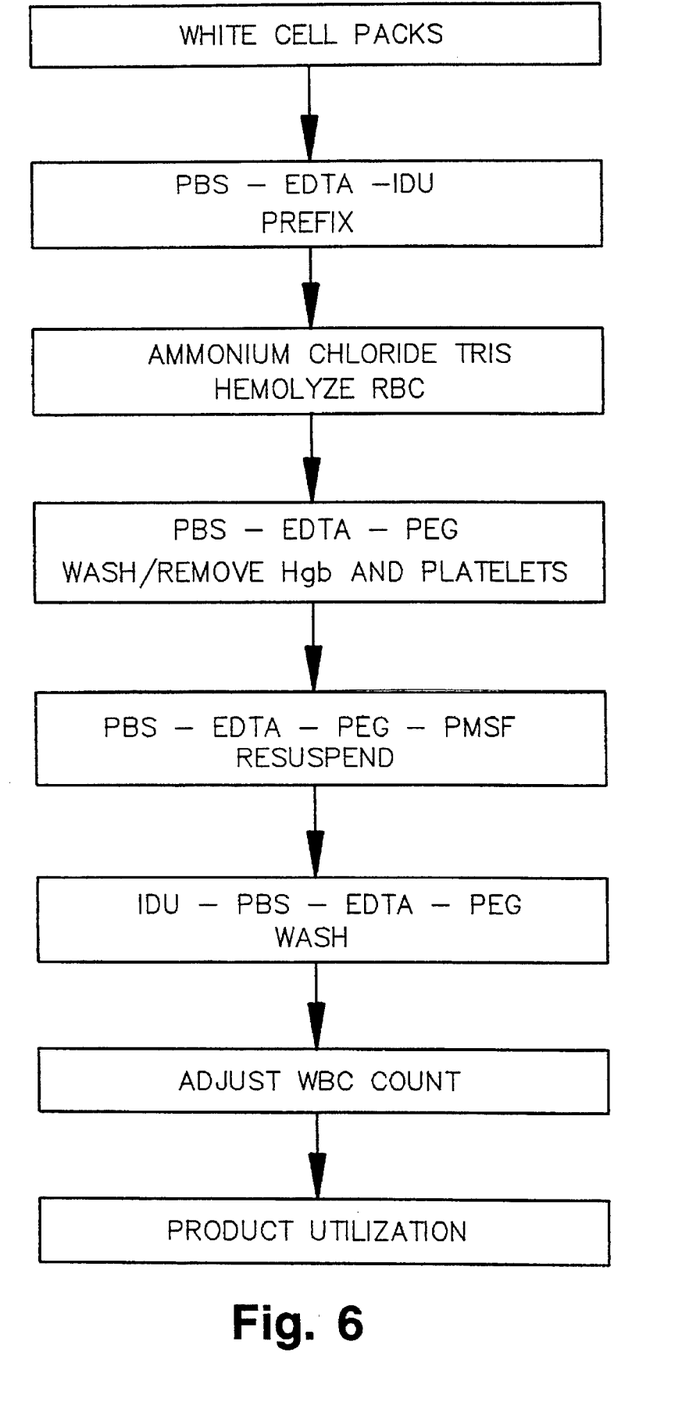
FIG. 6 is a flow diagram illustrating the procedure for preparing stabilized leukocytes subsets as a control.
Figure 7A:
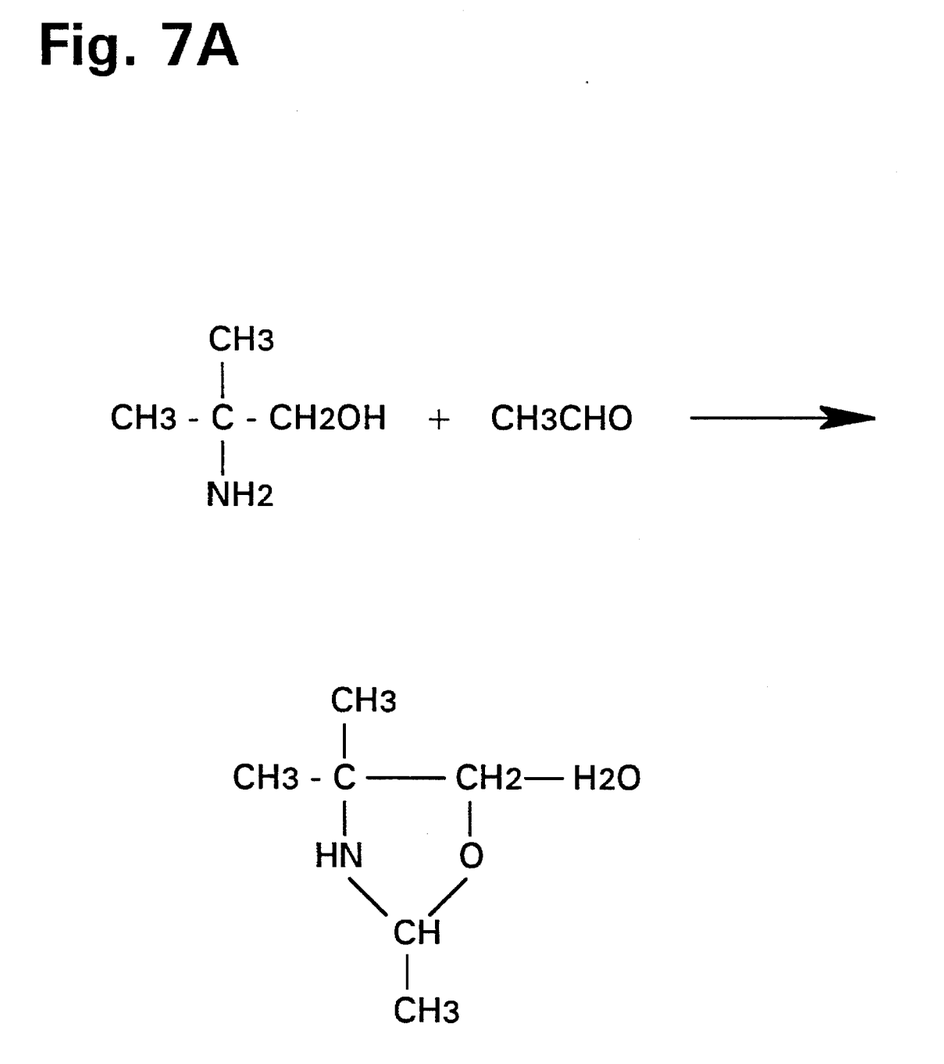
FIG. 7A shows the formation of oxazolidines.
Figure 7B:
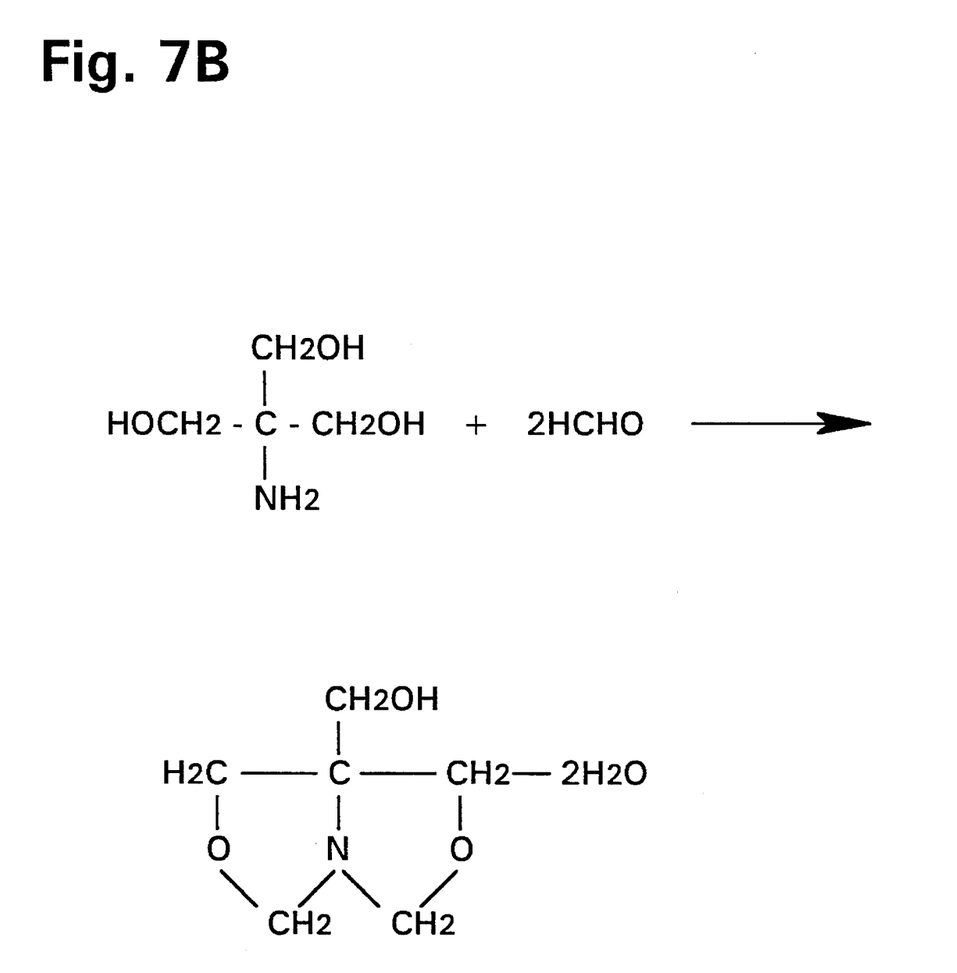
FIG. 7B shows the formation of oxazolidines.

Oxazolidines are formed by the reaction of amino alcohols with aldehydes. See FIG. 7A. Additionally, two moles of formaldehyde can react with amino alcohols to produce bicyclic oxazolidines. See FIG. 7B. These compounds can be used as cross-linking or curing agents in systems where aldehyde is normally used. More specifically, a list of representative oxazolidines is provided on page 26 of the specification.

A preferred fixative solution for tissues and cells comprises histological fixing amounts of the following ingredients:

i) diazolidinyl urea, ii) 2-bromo-2-nitropropane-1,3-diol ("BRONOPOL"), and iii) a water-soluble zinc salt in a solvent selected from the group consisting of water, alcohol, dimethylsulfoxide and mixtures thereof. In the preferred embodiment of this solution, the water-soluble zinc salt comprises zinc sulfate. If desired, the above fixative solution can be buffered to a pH of about 4–6 through the addition of a suitable buffer such as a citrate buffer.

In another aspect of the preferred embodiment, the invention comprises an improvement in a method of fixing tissues and cells with a histological fixative wherein the histological fixative is an active agent consisting of:

i) diazolidinyl urea, ii) 2-bromo-2-nitropropane-1,3-diol ("BRONOPOL"), and iii) a water-soluble zinc salt.

Unlike the typical histological fixing agents, the active agents of the invention have extremely low toxicity. For example, toxicity studies comparing diazolidinyl urea of the invention with formaldehyde of the prior art show the following:

|  | Inhalation Toxicity | Dermal Toxicity | LD50 |
| --- | --- | --- | --- |
| Formaldehyde | 500 mg/kg | 270 mg/kg | 800 mg/kg |
| Diazolidinyl urea | None | 2000 mg/kg | 2570 mg/kg |

This reduced toxicity makes disposal and handling less of a problem. In addition, since there is no inhalation toxicity, there are no badge detection devices required as there are for formaldehyde.

Another advantage offered by the active agents of the invention is the fact that they are not flammable and therefore do not present a fire hazard as do many of the prior art fixatives.

The mechanism by which the active agents of the invention provide the desired tissue and cell membrane stabilization is not known for certain. It is believed that the active agent binds in some fashion to the cell membrane or tissue. This hypothesis is drawn because many of the active agents of the invention are known disinfectants which kill bacteria by binding to cell structure. This is not a full explanation of the mechanism responsible for the results of the invention since many other disinfectants such as KATHON and OMADINE fail to provide tissue and cell stabilizing effects.

The ability of the active agents of the invention to preserve antigenic is also not understood but it is probably due to a difference in the reaction between proteins and the active agents of the invention compared to prior art fixatives such as formaldehyde. Formaldehyde cross-links with itself and proteins to obscure the antigen. To determine if this is true, diazolidinyl urea was added to the protein, albumin. After incubation of the diazolidinyl urea and protein mixture for 24 hours, disc-gel electrophoresis indicated no change in the rate of migration of the protein. When this experiment is conducted with formaldehyde, a large number of multimers and insoluble proteins result.

In another aspect of the invention, it has been found that the addition of alkali metal salts of ascorbic acid increases the activity of the active agents of the invention in fixing the tissue or cell membrane.

In yet another aspect of the invention, it has been found that the addition of glycine, or other formaldehyde reactive compounds, is useful in removing any free formaldehyde which may be an equilibrium component of the compositions of the instant invention. It should be noted, however, that the preferred compositions of the instant invention contain only trace amounts of formaldehyde in equilibrium.

In yet a further aspect of the invention, it should be understood that biological material fixed or stabilized by the composition and method of the instant invention need not be stored in the composition.

It should be noted that the process for fixing biological material described in the instant specification may be practiced by those skilled in the art to preserve antigenic sites on or within cells (or components thereof) derived from any source including normal blood, bone marrow, lymph, or solid tissues, or may be derived from abnormal tissues such as leukemias or solid tissue cancers. The present invention may also be utilized with any cellular component or biological material which has at least one antigenic site.

The active reagents of the instant invention are known to be formaldehyde donors. However, while not understood, it is known that the small amount of formaldehyde held in equilibrium with the reagent is not the active mechanism of the instant compositions.

It should be noted that in preferred embodiments of the present invention cell clumping is prevented, light scattering properties are preserved, antigenic sites are preserved, and nuclear DNA content may be analyzed.

BEST MODE FOR CARRYING OUT THE INVENTION

The fixative solutions of the invention are comprised of the active agents in a solvent selected from water, dimethylsulfoxide, alcohol and mixtures thereof.

The alcohol solvent comprises one or more alkanols such as methanol, ethanol, propanol, butanol, polyols, e.g., diols or triols such as ethylene glycol, glycerol, propylene glycol and trimethylene glycol and mixtures of alkanols and polyols. It is also preferable that a suitable buffer such as a citrate buffer may be added to the solution to adjust the pH to about 4–6. One particularly preferred citrate buffer to be used in the solution is sodium citrate dihydrate, but other buffers may be utilized as would be obvious to one skilled in the art.

Whether the solvent employed is water, alcohol, dimethylsulfoxide, or a mixture thereof, depends principally upon the tissue or membrane being fixed. For example, where large pieces of tissue are being fixed, it is preferred to use an alcohol solvent or aqueous alcohol solvent since the alcohol solvents increase penetration. Also, in fixing cells such as Pap smears, the alcoholic preparations are preferred because they cause the cells to adhere to slides. When aqueous alcoholic solutions are employed as the solvent for the active agent of the invention, the ratio of alcohol to water will fall approximately in the range of 4:1 to 2:1.

The amount of the active agents in the formulation of the invention is that effective to fix or stabilize the tissue or cell membrane. Generally, this amount falls in the range of about 5 to 100 grams per liter, preferably 50 to 75 grams per liter. Generally, in an exemplary embodiment the compositions are comprised of about 20–40 grams of 2-bromo-2-nitropropane- 1,3-diol (BRONOPOL) (about 30 grams particularly preferred), 20–40 grams of dizaolidinyl urea (about 30 grams particularly preferred) and about 10–15 grams of the water-soluble zinc salt (about 12 grams particularly preferred) per 1000 ml of solvent used. It is preferred that zinc sulfate, and more particularly zinc sulfate heptahydrate, be employed as the water-soluble zinc salt, but a number of other zinc salts will also be suitable as would be evident to one of ordinary skill in the art. For example, zinc salts such as zinc chloride or zinc acetate could also be employed, but these are considered less effective than zinc sulfate. In addition to the zinc salt, it is preferable to add about 2–6 grams of a citrate buffer (about 3 grams particularly preferred) such as sodium citrate dihydrate to the above fixative solution.

In terms of percentages, it is preferred that the fixative solution comprise about 1–5% BRONOPOL (about 3% particularly preferred) and about 1–6 diazolidinyl urea (about 3% particularly preferred). In an exemplary embodiment, about 0.2 to 0.1 g-mol/L zinc salt (about 0.05 particularly preferred) is added to the fixative solution along with the BRONOPOL and diazolidinyl urea.

When alkali metal ascorbic acid salts such as sodium ascorbate are included to increase the activity of the active agents to fix the tissue or cells, they are added in an amount of about 0.25 to 1 grams per liter.

The solute in the preparations of the invention may also include any of the other addendum conventionally added to histological fixative preparations. These addendum include mordants, buffers, penetration increasers, osmotically active substances and nuclear detail improves and nuclear size increasers.

Examples of suitable mordants are salts with a metal ion having an oxidation state of two or more. Illustrative are zinc, strontium, calcium, barium and chromium salts. The preferred salt is zinc sulfate.

Suitable buffers include alkali metal phosphate salts such sodium phosphate and potassium phosphate.

Osmotically active substances that may be included in the formulation of the invention are alkali metal salts such as sodium chloride. In addition, sugars such as the polysaccharides, sucrose, glucose and the like may be employed.

Nuclear detail improves and nuclear size increasers include acetic acid and lithium salts such as lithium chloride. Zinc salts such as zinc sulfate not only improve nuclear definition but also improve staining.

Illustrative of substances which increase the rate of penetration of the fixing agent are dimethylsulfoxide and ethanol.

In the preferred embodiment, the active fixative ingredients described above are dissolved in a suitable solvent such as distilled water, and this solution may then be used as a fixative agent in a number of ways as would be obvious to one skilled in the art. For example, the fixative solution may be used to preserve samples of tissues that are being shipped or carried to an examination site. In this process, small vials or jars that have liquid tight seals are filled with the reagent of the invention, and tissue samples are placed in the reagent-filled container to preserve the samples until they reach an area where further processing can occur.

Tissues prepared for study using the fixative of the invention may be prepared for histological study in any known convention manner, such as through the use of paraffin sectioning equipment, staining, mounting on slides, or other common steps utilized prior to microscopic or other examination. The present invention thus provides a safe, convenient and effective fixative solution which may be utilized in many known histological procedures that employ such solutions.

The following examples are illustrative of formulations of the invention.

EXAMPLE I

| | |
|---|---|
| Diazolidiyl urea | 50 g/L |
| Na$_2$HPO | 0.73 g/L |
| KHPO$_4$ | 0.02 g/L |
| NaCl | 8.50 g/L |
| Distilled H$_2$O to one liter | |

EXAMPLE II

| | |
|---|---|
| Diazolidinyl urea | 50 g/l |
| Ethanol | 500 ml |
| Acetic acid, conc. | 10 ml |
| Distilled H$_2$O to one liter | |

EXAMPLE III

| | |
|---|---|
| Diazolidinyl urea | 50 g/L |
| Lithium chloride | 6.35 g/L |
| Distilled H$_2$O to one liter | |

EXAMPLE IV

| | |
|---|---|
| Diazolidinyl urea | 50 g/L |
| Dimethylsulfoxide | 100 ml |
| Distilled H$_2$O to one liter | |

EXAMPLE V

| | |
|---|---|
| Diazolidinyl urea | 50 g/L |
| Dimethylsulfoxide | 100 ml |
| Zinc chloride | 5.8 g/L |
| Distilled H$_2$O to one liter | |

EXAMPLE VI

| | |
|---|---|
| Diazolidinyl urea | 50 g/L |
| Ascorbic acid, sodium | 0.25 g/L |
| Distilled H$_2$O to one liter | |

EXAMPLE VII

| | |
|---|---|
| Diazolidinyl urea | 1 g. |
| 2-bromo-2-nitropropane-1,3-diol | 1 g. |
| Tricholoracetic acid | 3 g. |
| Distilled water to one liter | |

EXAMPLE VIII

The following is an example of the use of fixatives of the invention.

Tissue is immersed in the fixative of Example I for four hours. The treated tissue is then dehydrated through a series of graded alcohols, cleared in xylene and impregnated with molten paraffin. This procedure is performed under heat and vacuum/pressure in a 12-hour cycle using a Fisher Histomatic (Model 166 MP) tissue processor. The tissue is then blocked, paraffin embedded, rehydrated in ice water for a minimum of three hours to enhance sectioning, and sectioned at 4–5 microns. The tissue is mounted on a glass slide, deparaffinized, stained, coverslipped and evaluated microscopically.

EXAMPLE IX

The following example demonstrates the satisfactory results obtained with the fixative of the invention using staining methods.

Example VII is repeated using the staining method identified below. The results in each case are as follows:

| Staining Method | Results |
|---|---|
| Mayer's mucicarmine | Demonstrable; well defined |
| Elastin | Satisfactory detail |
| Movat's reticulin stain | Satisfactory detail; minimal shrinkage |
| Gomori's trichrome | Fibrous tissue well |

| Staining Method | Results |
| --- | --- |
| stain | defined |
| Periodic Acid-Schiff (PAS) | Non-specific staining not evidenced as in formalin-fixed preparation |
| Geimsa | Satisfactory detail |
| Hematoxylin & eosin (H&E) | Satisfactory detail |

EXAMPLE X

The following example demonstrates the ability of the fixative of the invention in retaining tissue antigens in immunostaining procedures.

EXAMPLE The tissues identified below having the antigenic sites identified below are fixed with the fixative formulation of Example I and immunohistochemically stained using avidin-biotin staining.

| Tissue | Markers Detected |
| --- | --- |
| Lymph node | LN-1;LN-2;LN 3;UCA;L-26;LCHL-1 |
| Brain | Neurofilament; Glial Fibrillary Acidic Protein |
| Hodkings node | Ber $H_2$; Leu $M_1$ |
| Colon | Cytokertin MAK-6; Cytokeratin AE1/AE3 |
| Muscle | Desmin |
| Pituitary | S-100 |
| Breast | α-lactalbumin |
| Thyroid | Thyroglobulin |

EXAMPLE XI

A fixative in accordance with the present invention was prepared having the following formulation:

30 grams of BRONOPOL; 30 grams of Diazolidinyl urea; 12 grams of zinc sulfate heptahydrate; and 2.9 grams of sodium citrate dihydrate dissolved in 1000 ml distilled water.

This solution was used as a fixative for tissue samples by placing the samples in a vial containing the fixative solution, and holding the sample for about four hours in the fixative. After the tissue has been sufficiently treated with fixative, it is then dehydrated using a series of graded alcohols, cleared in xylene and impregnated with molten paraffin. This procedure is performed under heat and vacuum/pressure in a 12-hour cycle using a Fisher HISTOMATIC (Model 166MP) tissue processor. The tissue is then blocked, paraffin embedded, rehydrated in ice water for about three hours to enhance sectioning, and sectioned at 4–5 microns. The tissue is mounted on a glass slide, deparaffinized, stained, coverslipped and evaluated microscopically.

Through use of the composition and method of the present invention, satisfactory results have been obtained with a variety of staining methods. The following results have been obtained using the fixative of the invention:

| Staining Method | Results |
| --- | --- |
| Mayer's mucicarmine | Demonstrable; well-defined |

| Staining Method | Results |
| --- | --- |
| Elastin | Satisfactory detail |
| Movat's reticulin stain | Satisfactory detail; minimal shrinkage |
| Gomori's trichrome stain | Fibrous tissue well-defined |
| Periodic Acid-Schiff (PAS) | Non-specific staining not evidenced as in formalin-fixed preparation |
| Hematoxylin & eosin (H&E) | Satisfactory detail |
| Geimsa | Factory detail |

EXAMPLE XII

The tissues identified below having the antigenic sites identified below are fixed with the fixative formulation of Example X and immunohistochemically stained using avidin-biotin staining.

| Tissue | Markers Detected |
| --- | --- |
| Lymph node | LN-1;LN-2;LN-3;LCA;L-26;UCHL-1;B72.3 |
| Brain | Neurofilament; Glial Fibrillary Acidic Protein; Vimentin |
| Hodgkin's node | Ber $H_2$; Leu $M_1$ |
| Muscle | Desmin; Smooth Muscle Actin |
| Pituitary | S-100 |
| Thyroid | Thyroglobulin |
| Breast | α-lactalbumin; Estrogen Receptors (ER's); Progesterone Receptors (PRs) |
| Skin | HMB 45 Melanoma |
| Colon | Cytokeratin MAK-6; Cytokeratin AE1/AE3; Epithelial Membrane Ag (EMA) |

None of the antigenic sites are affected by the immunostaining.

EXAMPLE XIII

Leukocyte Positive Control Check for Antigen-Antibody Studies. Positive control methods are needed to verify the performance of reagents, preparation methods, staining procedures as well as the performance of the flow cytometer instrumentation itself. This requires a preparation of human white blood cells, preferably with a mixed distribution of leukocytes (lymphocytes, monocytes, and granulocytes), to evaluate the performance of the procedure before it is used to evaluate subject tissues, cells, or cell components. While much of the methodology used in this procedure is familiar to those skilled in the art, this invention is novel in its use of imidazolidinyl urea (IDU) as a cell stabilizer, the use of polyethylene glycol to reduce damage to the white blood cells during processing, the use of PMSF to inhibit protease activity, and the process itself.

The invention discloses a new method of producing a positive control check material with significant advances over the prior art. Production is begun by placing one pack of human white blood cells, obtainable from commercial blood banks, in each bottle of the centrifuge. Samples from each pack are placed into a plastic tube for screening on the flow cytometer. Because of the considerable variation from donor to donor in cluster designation antigen sites, only packs with similar properties are pooled. Each product pool should be limited to a particular ABO blood type to prevent clumping as a result of a histoin-compatibility reaction between the cells. The samples are placed into plastic tubes rather than glass because unfixed white blood cells may be activated by the glass causing them to adhere to the glass and each other.

The cells are prefixed 1:1 with 1% IDU in phosphate buffered saline ethylenediaminetetraacetic acid (PBS-EDTA) at 6° C. for one hour. This acts to stabilize the white blood cells without interfering with the lysis of the red blood cells. The cells and all diluents used in the processing must be kept at 6° C. at all times by use of refrigeration and a chiller bath to reduce the amount of cell damage which alters the scattergram.

The bottle are next centrifuged at 900 rpm for 10 minutes, and the supernatant is removed. This angular velocity is sufficient to pellet the white blood cells without damaging them. Ammonium chloride tris, 200 ml/bottle set at 6° C. for 20–30 minutes, is then used to lyse the red blood cells.

A second centrifugation follows, again at 900 rpm for 10 minutes, and the supernatant is removed. Next 250 ml/bottle of ammonium chloride tris are added at 6° C. or 45–60 minutes, with 60 minutes usually ensuring complete lysis of the red blood cells.

The material is then centrifuged a third time at 900 rpm for 10 minutes and then the supernatant is removed. If the cell pellets still contain red blood cells, add 150 ml/bottle of ammonium chloride tris at 6° C. for 20 to 30 minutes and centrifuge a fourth time at 900 rpm for 10 minutes and remove the supernatant.

The cells are then washed three times with PBS/EDTA/1% polyethylene glycol (PEG) 20,000 by centrifuging at 900 rpm for 10 minutes and removing the supernatant.

After the final wash, each bottle is resuspended with 100 ml of PBS/EDTA/0.3% PEG/3% IDU/2mM phenylmethylsulfonyl fluoride (PMSF) and set at 6° C. for 2 days. Fixation with 3% IDU stabilizes the cells for use on the flow cytometer, with lower concentrations of IDU reducing stability and higher concentrations causing cells to lose the cluster designation marker and produce scatterplot changes. Next each bottle is washed two times with PBS/EDTA/0.3%PEG/IDU to remove PMSF and residual platelets.

Finally, the white blood cell count of each bottle selected for final pooling should be adjusted to meet the final product specifications. These counts may be performed on the ELT 1500 or ZBI, in triplicate, prior to pooling.

The product is now ready for use in aiding laboratory studies in that a desired reagent may be combined with the product and then examined with a flow cytometer to establish a normal baseline for the evaluation of subject tissue, cells, and cell components.

The product prepared according to this procedure may be utilized to analyze more antibodies since it contains lymphocytes, monocytes, and granulocytes. Thus, the product of this process is a more complete control and all WBC's produce a scattergram similar to that of whole blood.

Product reproduced by the before mentioned procedure has a seven day open and 90 day closed vial stability, does not have to be reconstituted, is compatible with all major flow cytometry systems, and one product may be utilized to monitor several areas of quality control.

The present invention has several advantages over prior art controls. For example, the prior art controls: (1) do not resemble human specimens, i.e., size, shape and granularity; (2) have short open vial stability (24 hours); (3) are lyophilized and must be reconstituted; and (4) cannot be utilized to test lyse procedures. It should be noted that red blood cells can be added to the positive control to form a multipurpose control.

EXAMPLE XIV

Indirect Immunofluorescence Staining of Cell Surfaces. The indirect method of immunofluorescence staining of cell surfaces may be used to enhance the fluorescence signal, and may also be utilized with the present invention to enhance its function as a positive control check. Since indirect methods will alter the proportionality between the amount of antigen and the fluorescence intensity per cell, these methods are not recommended for assessing the absolute number of antigenic determinants per cell, but are effective in determining the relative quantitative differences between control and subject cell populations.

EXAMPLE XV

Direct Immunofluorescence Staining of Cell Surfaces. This method is used to detect cells bearing specific membrane antigens by treating a cell population with monoclonal antibodies conjugated to fluorescein or phycoerythrin, and is recommended for analysis by flow cytometry or fluorescence microscopy. The use of the present invention control procedure is ideally suited to the direct immunofluorescence staining method in establishing a quality control program for laboratory reagents, procedures, and flow cytometers.

EXAMPLE XVI

Tumor Immunization. 6C3HED lymphosarcoma was grown in C3H mice as ascites (ascites cause collection of fluid in the peritoneal cavity). The ascites cells were then washed in phosphate buffered saline (PBS) containing 3% IDU, 3% Glydant, or 3% Dimethylol urea. The cells were then placed at 6° C. for 48 hours. Vital staining indicated that none of the cells were viable.

As a control for immunization, cells were also washed into PBS containing 3% para formaldehyde and held under the same conditions. After 48 hours, all the cell groups were washed into PBS to remove the fixatives. The cell count was adjusted to 200,000/ml. Five C3H mice were injected with each of the cell groups for the first immunization. The procedure was repeated two weeks later.

The immunized mice were challenged with 100,000 viable 63HED ascites cells by intraperitoneal injection. The efficacy of the immunization was determined by the average death time for each group of mice.

| | | Average Death Days |
|---|---|---|
| A. | Control | 10 days |
| B. | IDU | No deaths at 65 days |
| C. | Glydant | No deaths at 65 days |
| D. | Dimethylol urea | No deaths at 65 days |

Tetanus toxin must be treated before it can be used to immunize. This is currently done with formalin. Swiss mice were inoculated intraperitoneally with tetanus toxin prepared by inactivation with IDU or formalin. The level of IDU used can be 1% or greater, but for this experiment, a 5% solution (final) was used to inactivate the toxin. The antibody levels were measured at 14 and 28 days.

|       | 14 Days | 28 Days |
| ----- | ------- | ------- |
| IDU   | 200     | 560     |

These values set forth the percent increase in antibody titer over formalin.

It should be noted that the concentration range for the active ingredient is best established in order to preserve antigenic sites by setting a low-end which preserves the cell or protein and also preserves the physical properties of cell size and granularity. The upper-end is set so as to preserve the antigenic sites and provide reproducible results over time.

General Information

A 6% w/v solution of each compound was used and samples tested at 24 hours (22° C). WBC's autolyse though RBC's do not. Relative RBC fixation was detected by adding known RBC lysing agent. WBC's are fixed if these cells do not disintegrate or clump over a period of approximately two hours after removal of compound. Fixing is relative and depends on how long you want cells or tissues to remain fixed. Structures:

1) Bronopol: 2-bromo-2-nitropropane-1, 3-diol. Synthesized from p-formaldehyde and nitromethane, then bromated. Decomposition liberates formaldehyde. Fixes both RBC's and WBC's.

2) Imidazolidinyl urea: Synthesized by reaction of alantoin and formaldehyde. Decomposition releases formaldehyde. Fixes both RBC's and WBC's.

3) Diazolidinyl urea: Synthesized by reaction of allantoin and formaldehyde. Contains 1–2 ppm of formaldehyde. Fixes both RBC's and WBC's.

4) Glydant: Dimethylol-5, 5-dimethylhydantoin, a formaldehyde derivative. Solution contains 2.1% formaldehyde. Fixes both RBC's and WBC's.

5) Dimethylol urea: Synthesized from urea and formaldehyde. Formaldehyde is released in very small quantities. Fixes both RBC's and WBC's.

6) Oxazolidines:

The following is a list of oxazolidines by tradename. The active ingredients in each of these compounds are listed. It is understood that as purchased these compounds may contain other ingredient such as water.

i) NUOSEPT 95 (HÜLS America, Inc.)
   24.5% by weight—5-Hydroxymethoxymethyl-1-aza-3,7-dioxabicyclo (3.3.0) octane
   17.7% by weight —5-Hydroxymethyl-1-aza-3,7-dioxabicyclo (3.3.0) octane
   7.8% by weight—5-Hydroxypoly [methyleneoxy]methyl-1-aza-3,7-dioxabicyclo (3.3.0) octane.

ii) NUOSEPT 145 (HÜLS America, Inc.)
   50% by volume—[1-methyl-2-(5-methyl-3-oxazolidinyl)-ethoxy] methoxy]methanol iii) NUOSEPT 65 (HÜLS America, Inc.)
   74.7% by weight—4,4-dimethyloxazolidine
   2.5% by weight—3,4,4-trimethyloxazolidine iv) OXABAN-A (Angus Chemical Co.)
   76.0% by weight—4,4-Dimethyloxazolidine
   >1.0% by weight—3,4,4-Trimethyloxazolidine
   <1.5% by weight—2-amino-2-methyl-1-proponal v) OXABAN-E (Angus Chemical Co.)
   96% by weight—7A-Ethyldihydro-1H,3H,5H-Oxazolo (3,4-C) Oxazolo
   2% by weight—4,4-dimethyl-oxazolidine and 4-ethyl-oxazolidine vi) Amine CS-1135 (Angus Chemical Co.)
   76% by weight—4,4-dimethyl-1-oxa-3-azacyclopentane
   >1.0% by weight—3,4,4-trimethyl-1-oxa-3-azacylopentane
   ±1.5% by weight 2-Amino-2-methyl-1-propanol vii) Amine CS-1246 (Angus Chemical Co.)
   96% by weight—7A-Ethyldihydro-1H,3H,5H-Oxazolo (3,4-C) Oxazolo
   2% by weight—4,4-dimethyl-oxazolidine and 4-ethyl-oxazolidine viii) ZOLDINE ZE (Angus Chemical Co.)
   96% by weight—7A-Ethyldihydro-1H,3H,5H-Oxazolo (3,4-C) Oxazolo
   2% by weight—4,4-dimethyl-oxazolidine and 4-ethyl-oxazolidine vix) ZOLDINE ZT-55 (Angus Chemical Co.)
   55.0% by weight—5-hydroxymethyl-1-aza-3,7-dioxabicyclo (3,3,0) octane 7) Suttocide: Sodium hydroxymethyl glycinate. Derivative of glycine. Fixes RBC's and WBC's. Contains 1% formaldehyde.

All of the disinfectants described as cell fixatives or stabilizers may be used to fix cells or tissues. The concentration and additives ($ZnSO_4$, ethylene glycol, etc.) will vary depending upon the circumstances of use. The characteristics of all of the above disinfectant compounds are:

a) they contain formaldehyde as an equilibrium component, b) they can be synthesized from formaldehyde, c) they are chemical disinfectants, d) they are capable of undergoing hydrogen bonding, and e) they function to fix or stabilize with from between 5 to 100 grams of agent per liter.

In addition, the agents can also be characterized in that they function to fix or stabilize at concentrations from about two to sixty times their usual concentration as bactericide.

Our studies with cells indicates fixing and stabilizing activity is not due to free formaldehyde, i.e., when compounds which react readily with the free formaldehyde are added, the tissue fixation still occurs. Example of these formaldehyde reactive compounds are glycine, allantoin, and sulfites.

Whereas, the invention has been described in connection with preferred embodiments and procedures thereof, it is apparent that many additions, modifications and substitutions may be made which are within the intended broad scope of the appended claims.

Thus there has been shown and described an improved composition, method and process which accomplishes at least all of the stated objects.

We claim:

1. In a method for the analysis of a biological material wherein said biological material is a cell or tissue preserved by a fixing or stabilizing solution, the improvement comprising: treating said biological material with a fixative which comprises at least one oxazolidine in an amount sufficient to fix said biological material; and analyzing said preserved biological material.

2. The method of claim 1, wherein the oxazolidine is selected from the group consisting of:

1) 24.5% by weight 5-hydroxymethoxymethyl-1-aza-3,7- dioxabicyclo (3.3.0) octane, 17.7% by weight 5-hydroxymethyl-1-aza-3,7-dioxabicyclo (3.3.0) octane, 7.8% by weight 5-hydroxypoly methyl-1-aza-3, 7-dioxabicyclo (3.3.0) octane;

2) 50% by volume [[1-methyl-2-(5-methyl-3-oxazolidinyl)ethoxy ]methoxy]methanol;

3) 74.7% by weight 4,4-dimethyloxazolidine, 2.5% by weight 3,4,4-trimethyloxazolidine;

4) 76.0% by weight 4,4-dimethyloxazolidine, greater than 1.0% by weight 3,4,4-trimethyloxazolidine, less than 1.5% by weight 2-amino-2-methyl-1-propanol;

5) 96% by weight 7A-ethyldihydro-1H, 3H, 5H-oxazolo (3,4-C) oxazolo, 2% by weight 4,4-dimethyl-oxazolidine and 4-ethyl-oxazolidine;

6) 76% by weight 4,4-dimethyl-1-oxa-3-azacyclopentane, greater than 1.0% by weight 3,4,4-trimethyl-1-oxa-3-azacyclopentane, greater than or equal to 1.5% by weight 2-amino-2-methyl-1-propanol;

7) 96% by weight 7A-ethyldihydro-1H,3H,5H-oxazolo (3,4-C) oxazolo, 2% by weight 4,4-dimethyl-oxazolidine and 4-ethyl-oxazolidine;

8) 96% by weight 7A-ethylodihydro-1H,3H,5H-oxazolo (3,4-C) oxazolo, 2% by weight 4,4-dimethyl-oxazolidine and 4-ethyl-oxazolidine; and 9) 55.0% by weight 5-hydroxymethyl-1-aza-3, 7-dioxabicyclo (3,3,0) octane.

3. The method of claim 1, wherein the oxazolidine is present in an amount of about 5 to about 100 grams per liter.

4. The method of claim 1, wherein the fixing or stabilizing solution further comprises water.

5. The method of claim 1, wherein the fixing or stabilizing solution further comprises alcohol.

6. The method of claim 1, wherein the fixing or stabilizing solution further comprises about 0.25 to about 1 grams per liter of an alkali metal salt of ascorbic acid.

7. The method of claim 6, wherein the salt is sodium ascorbate.

8. The method of claim 1, wherein the fixing or stabilizing solution further comprises acetic acid in an amount sufficient to improve nuclear detail.

9. The method of claim 1, wherein the fixing or stabilizing solution further comprises dimethylsulfoxide in an amount sufficient to increase the rate of penetration of the oxazolidine.

10. The method of claim 1, wherein the fixing or stabilizing solution further comprises zinc sulfate in an amount sufficient to improve staining and nuclear detail.

\* \* \* \* \*